(12) United States Patent
Decock et al.

(10) Patent No.: US 10,160,577 B2
(45) Date of Patent: Dec. 25, 2018

(54) LIQUID-DISPENSING DEVICE COMPRISING A PROTECTIVE CAP

(71) Applicant: Nemera La Verpillière S.A.S., La Verpilliere (FR)

(72) Inventors: Thierry Decock, Lyons (FR); Gaëtan Painchaud, Francheville (FR); Benjamin Quaglia, Lyons (FR)

(73) Assignee: Nemera La Verpillière (FR)

( * ) Notice: Subject to any disclaimer, the term of this patent is extended or adjusted under 35 U.S.C. 154(b) by 0 days.

(21) Appl. No.: 15/127,677

(22) PCT Filed: Mar. 19, 2015

(86) PCT No.: PCT/FR2015/050680
§ 371 (c)(1),
(2) Date: Sep. 20, 2016

(87) PCT Pub. No.: WO2015/140473
PCT Pub. Date: Sep. 24, 2015

(65) Prior Publication Data
US 2017/0129662 A1    May 11, 2017

(30) Foreign Application Priority Data
Mar. 20, 2014    (FR) .................... 14 52341

(51) Int. Cl.
| B65D 47/40 | (2006.01) |
| B05B 14/00 | (2018.01) |
| B05B 15/52 | (2018.01) |
| B05B 11/00 | (2006.01) |
| B05B 11/02 | (2006.01) |

(Continued)

(52) U.S. Cl.
CPC ............. *B65D 47/40* (2013.01); *A61M 11/00* (2013.01); *B05B 11/0032* (2013.01); *B05B 11/02* (2013.01); *B05B 11/04* (2013.01); *B05B 14/00* (2018.02); *B05B 15/52* (2018.02); *B65D 47/2081* (2013.01); *B65D 83/14* (2013.01); *B65D 83/34* (2013.01); *B65D 83/40* (2013.01);

(Continued)

(58) Field of Classification Search
CPC ...................................................... B65D 47/40
See application file for complete search history.

(56) References Cited

U.S. PATENT DOCUMENTS

| 2,579,202 | A | * | 12/1951 | Piccoli | .................. | A45D 34/04 |
| | | | | | | 215/232 |
| 3,628,697 | A | * | 12/1971 | Dowson | ................. | B65D 23/06 |
| | | | | | | 222/111 |

(Continued)

FOREIGN PATENT DOCUMENTS

| EP | 1661818 A1 | 5/2006 |
| EP | 2537773 A1 | 12/2012 |

(Continued)

*Primary Examiner* — J. Casimer Jacyna
(74) *Attorney, Agent, or Firm* — St. Onge Steward Johnston & Reens, LLC (57) ABSTRACT

A liquid-dispensing device including a cap for protecting a liquid-dispensing opening, the protective cap being provided with a pad for absorbing residual liquid, made of an absorbent material, the absorbent pad being fastened to a support made of a more resistant material than the absorbent pad, the support being furthermore fastened in the protective cap.

19 Claims, 6 Drawing Sheets

(51) Int. Cl.
*B05B 11/04* (2006.01)
*B65D 83/14* (2006.01)
*B65D 83/34* (2006.01)
*B65D 83/40* (2006.01)
*B65D 47/20* (2006.01)
*A61M 11/00* (2006.01)
*B05B 15/40* (2018.01)

(52) U.S. Cl.
CPC ......... *B05B 11/007* (2013.01); *B05B 11/0072* (2013.01); *B05B 15/40* (2018.02)

(56) References Cited

U.S. PATENT DOCUMENTS

| | | | | |
|---|---|---|---|---|
| 6,248,085 | B1 * | 6/2001 | Scholz | A61M 35/006 118/266 |
| 8,007,480 | B2 * | 8/2011 | Kawashiro | A61F 9/0008 604/289 |
| 9,592,934 | B2 * | 3/2017 | Painchaud | B05B 11/00 |
| 2010/0096416 | A1 | 4/2010 | Painchaud et al. | |
| 2011/0125111 | A1 * | 5/2011 | Chibret | A61F 9/0008 604/300 |
| 2012/0187154 | A1 * | 7/2012 | Benson | B05B 11/0043 222/402.12 |
| 2013/0134186 | A1 * | 5/2013 | Defemme | B65D 47/18 222/321.1 |
| 2013/0200099 | A1 * | 8/2013 | Abe | B65D 35/14 222/95 |
| 2014/0124537 | A1 * | 5/2014 | Urquhart | B05B 15/025 222/148 |
| 2015/0043958 | A1 * | 2/2015 | Painchaud | B05B 11/00 401/262 |

FOREIGN PATENT DOCUMENTS

| | | |
|---|---|---|
| FR | 2988015 A1 | 9/2013 |
| JP | H09150855 A | 6/1997 |
| JP | 2000159259 A | 6/2000 |
| JP | 2010131370 A | 6/2010 |
| JP | 2013542854 A | 11/2013 |
| WO | 2012100013 A1 | 7/2012 |
| WO | 2013140069 A1 | 9/2013 |

* cited by examiner

LIQUID-DISPENSING DEVICE COMPRISING A PROTECTIVE CAP

FIELD OF THE INVENTION

The present invention relates to the technical field of liquid dispensing. In particular, but not exclusively, it relates to the field of the dispensing of liquid in the form of drops or in the form of spray, such as ophthalmic, nasal, buccal or auricular liquid.

BACKGROUND OF THE INVENTION

From the prior art, for example from the document FR 2 988 015, a liquid-dispensing device is known that comprises a flask, a dispensing end piece provided with a liquid-dispensing opening and a removable cap protecting this opening. The protective cap comprises an absorption pad, made in such a way that residual liquid is absorbed by the pad, thus making it possible to limit the subsequent administration of contaminated residual liquid.

It has been found that, during the process of mounting the absorption pad inside the protective cap, particles originating from the pad can be generated, notably by friction occurring during the manipulation of the pad on the protective cap. Now, these particles can be the source of product contamination, or even of the administration of particles to the eye. Furthermore, these particles are likely to build up in different parts of the device, for example by being deposited on the absorption pad, inside the device, with the risk of creating a malfunction of a non-return valve, or even in a device assembly white room, a room in which the rate of particles present inside is the subject of regulations and controls.

SUMMARY OF THE INVENTION

The aim of the present invention is notably to provide a liquid-dispensing device that further prevents the contamination of the product dispensed.

To this end, the subject of the invention is a liquid-dispensing device comprising a protective cap for a liquid-dispensing opening, the protective cap being provided with a residual liquid absorption pad, made of an absorbent material, the absorption pad being fixed onto a support made of a stronger material than the absorption pad, this support being also fixed in the protective cap.

Thus, the absorption pad is fixed onto the protective cap via the support. It is proposed to fix the pad onto a support, which makes it possible to reduce, even totally limit, the generation of particles which could occur when mounting the pad in the protective cap. In effect, since the pad is generally made of a relatively brittle material, the fact that it is fixed onto a support rather than directly onto the protective cap means that, in the case where particles might be generated when fixing the absorption pad in the support, these particles can then be removed, and are not jammed inside the protective cap. Moreover, since the support is made of a stronger material than the absorption pad, the forces which are exerted by the protective cap on the absorption pad during assembly are applied to the support, which generates fewer particles, because there is no longer, or almost no longer, friction between the absorption pad and the protective cap during assembly. Consequently, a device is obtained which limits the quantity of particles likely to contaminate the product to be administered and which reduces the risk of accidentally administering particles into the eye that can be harmful, objectionable and/or that makes it possible to observe certain regulatory constraints.

It will therefore be understood that the lateral edge of the absorption pad is spaced apart from centering outlines of the absorption pad in the protective cap, so that the contacts and/or friction are avoided between the absorption pad and the centering outlines, therefore between the absorption pad and the protective cap. There is therefore little or no formation of particles when adding the support provided with the absorption pad into the protective cap.

The spacing means for the lateral edge of the absorption pad are borne by the support, for example by the lateral walls of the support.

"Materials stronger than the absorption pad" should be understood to mean a material that is more cohesive than that of the absorption pad, that is to say that the forces of interaction within the substance of the support are stronger than those within the substance of the absorption pad, in particular the forces of electromagnetic interaction. Since the support is made of a stronger material, it exhibits reduced brittleness and increased resistance to friction, and therefore makes it possible to limit the generation of particles. For example, the support is made of plastic material such as polyethylene (PE), and the absorption pad is made of a material comprising at least one hydrophilic part, making it possible to drain liquid, that is to say capable of absorbing liquid, even of allowing it to evaporate if an evaporation path is open.

The device presented above can further comprise one or more of the following features, taken alone or in combination.

The support is made of plastic material, such as polyethylene. The plastic material offers a better resistance to the support than to the absorption pad, so as to limit the generation of particles under the effect of friction which could occur during mounting.

The support has an annular form. This annular form makes it possible to limit the friction over the entire perimeter of the absorption pad.

The support extends over the entire height of the absorption pad. This thus makes it possible to restrict or eliminate any part of the absorption pad in contact with the protective cap.

The residual liquid absorption pad is fixed onto the support by overmolding. The overmolding of the absorption pad on the support or of the support on the absorption pad offers the advantage of not generating any particles during assembly, and further makes it possible to ensure unicity in the assembly comprising the support and the absorption pad, to allow for a better cohesion between these two parts.

The absorption pad is fixed onto the support, by clamping, snap-fitting, bonding or placed on the support in such a way that the absorption pad is held on the support. Such an assembly is particularly simple to implement.

The absorption pad is made of a porous material. Thus, the porous material makes it possible to have satisfactory absorption properties, in particular hydrophilic properties, useful for the absorption of the residual liquid by the absorption pad, so as to obtain an almost complete or complete absorption of the residual liquid by the pad. Furthermore, it can allow protection against any microbial contaminations by virtue of the absorption, draining and drying of the residual liquid due to the porous nature of the material.

The absorption pad comprises woven or unwoven materials. It can for example comprise hydrophilic cotton, polyethylene (PE) that has undergone a hydrophilic treatment, polyethylene terephthalate (PET) that has undergone a hydrophilic treatment, a poly(vinyl acetate) (PVA) foam or even a mixture of a number of hydrophilic materials.

The absorption pad is made of a material comprising ethylene vinyl acetate (EVA). The use of this material to produce the absorption pad is particularly advantageous because it makes it possible to limit the formation of particles. In effect, the structure of the EVA, in foam form, has a better cohesion than that of the absorption pad, while maintaining the absorbent properties thereof.

The absorption pad is a multilayer pad. The layers are preferably stacked axially on top of one another. In particular, the absorption pad can comprise at least two distinct absorbent materials, arranged one on top of the other, the downstream material being more hydrophilic than the upstream material. Thus, the liquid is sucked up by the more hydrophilic material and the residual liquid does not stagnate in the less hydrophilic material arranged in proximity to the dispensing opening. The residual drop is thus entirely absorbed by virtue of the proximity of the absorption pad. The upstream material advantageously comprises a hydrophobic material. It therefore prevents the liquid absorbed by the more hydrophilic material from returning to the dispensing opening. The absorption pad can further comprise, on at least one of its layers, an antimicrobial agent which can be of disinfectant or bacteriostatic type. The advantage of such an absorption pad is a very great microbial efficiency, without this microbial agent coming into contact with the liquid delivered.

The surface area of the absorption pad in contact with the air can be increased, notably to speed up the rate of drying of the pad, in particular when a low-absorption pad is used.

The absorption pad is kept immobile between two axial abutments of the support cooperating with the absorption pad. The absorption pad is immobilized by axial pinching between the axial abutments of the support. The risk of friction between the absorption pad and the support is thus reduced.

The support comprises two parts fitted into one another, each part defining an axial abutment. This embodiment is simple to implement.

The support is fixed in the protective cap by mechanical assembly, for example by clamping or by snap-fitting, possibly via one or more reliefs or hollows, continuous or not, such as a ridge or a stud, formed on the protective cap and/or the support. Thus, after insertion of the support by forcing it into the protective cap and elastic deformation of the support on passing the relief or reliefs, the relief and/or the hollow can form a mechanical abutment of the support in the protective cap. It is also possible to provide a relief of different geometry capable of exerting a function of blocking of the support relative to the protective cap. It is also possible to glue the support in the protective cap. Thus, the assembly will be able to be handled and assembled with other parts while minimizing any possible disassembly of the protective cap and of the support on which the absorption pad is fixed.

The device comprises a residual liquid expulsion form situated in the immediate vicinity of and facing the dispensing opening and borne by the protective cap or the support, when the protective cap is mounted on the device. The expulsion form expels most of the residual liquid present downstream of the dispensing opening, notably toward the residual liquid absorption pad arranged in proximity, that is to say that the residual liquid is discharged toward the absorption pad. It will therefore be understood that the absorption pad is arranged downstream of the dispensing opening. Thus, a draining of most of the residual liquid out of the dispensing opening is produced. The expulsion or discharging of residual liquid in the vicinity of the dispensing opening avoids the development of bacteria in this zone, which is particularly advantageous when the liquid dispensed does not include any conserving agents.

The device can take, when the protective cap is mounted on the device, a configuration of hermetic closure of the device, before its first use, in which the residual liquid evaporation path is closed between the absorption pad and the outside of the device, and a configuration of ventilation of the device, in which the evaporation path is open between the absorption pad and the outside.

The device comprises a residual liquid evaporation path between the absorption pad and the outside of the device when the protective cap is mounted on the device, the protective cap comprising an outer casing and an inner casing, mounted mobile relative to one another between a first configuration, corresponding to a configuration of hermetic closure of the device, and a second configuration corresponding to a configuration of ventilation of the device, in which the evaporation path is open between the absorption pad and the outside. Thus, the protective cap allows a ventilation as described in the document FR 2 988 015, so that the residual liquid absorbed by the absorption pad can be evaporated out of the device.

The protective cap comprises air passage orifices and a seal closing the residual liquid evaporation path before the first use. The seal is removable, preferably disposable, and is added onto the protective cap. Upon first use, the user removes the seal from the device which passes from the configuration of hermetic closure to the configuration of ventilation.

Also a subject of the present invention is a method for assembling a device as presented previously, during which the absorption pad and the support are first of all assembled, then the assembly is added into the protective cap, the method preferably further comprising a step of blowing of compressed air over the assembly of the absorption pad and the support, before they are added into the protective cap. With the absorption pad being previously assembled with the support separately, the generation of particles in the device is thus minimized. Furthermore, the generation of particles in the device is also minimized when the absorption pad and support assembly is assembled on the protective cap. Finally, the optional additional blowing step advantageously makes it possible to eliminate any particle which might have been generated.

BRIEF DESCRIPTION OF THE DRAWINGS

The invention will be better understood on reading the attached figures, which are supplied as examples and are in no way limiting, in which.

DETAILED DESCRIPTION OF THE INVENTION

Figure 1:
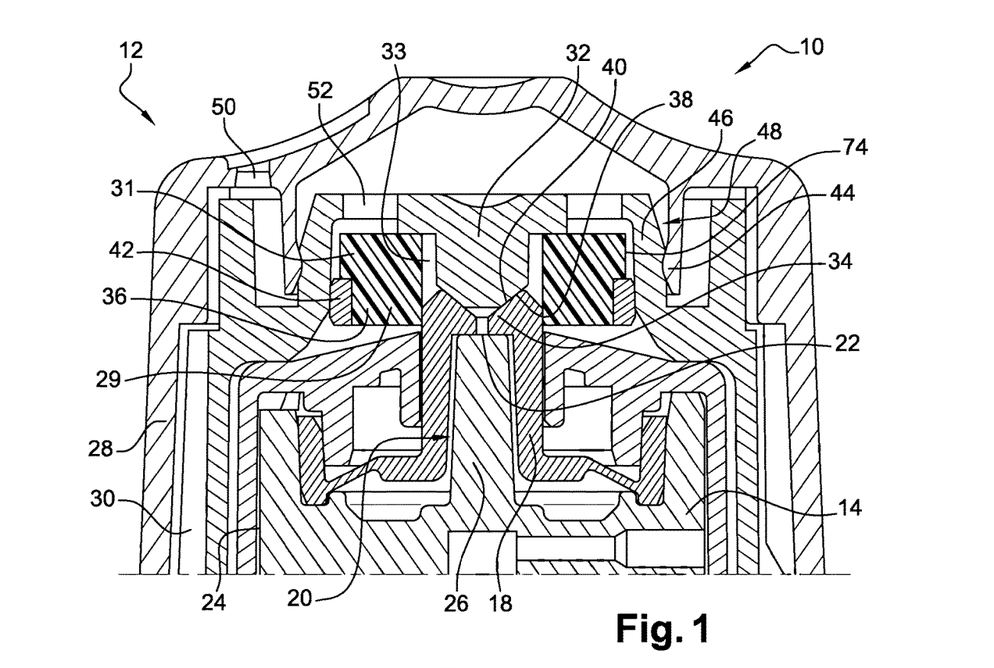
FIG. 1 is a longitudinal cross-sectional view of a dispensing device according to a first embodiment.
Figure 2:
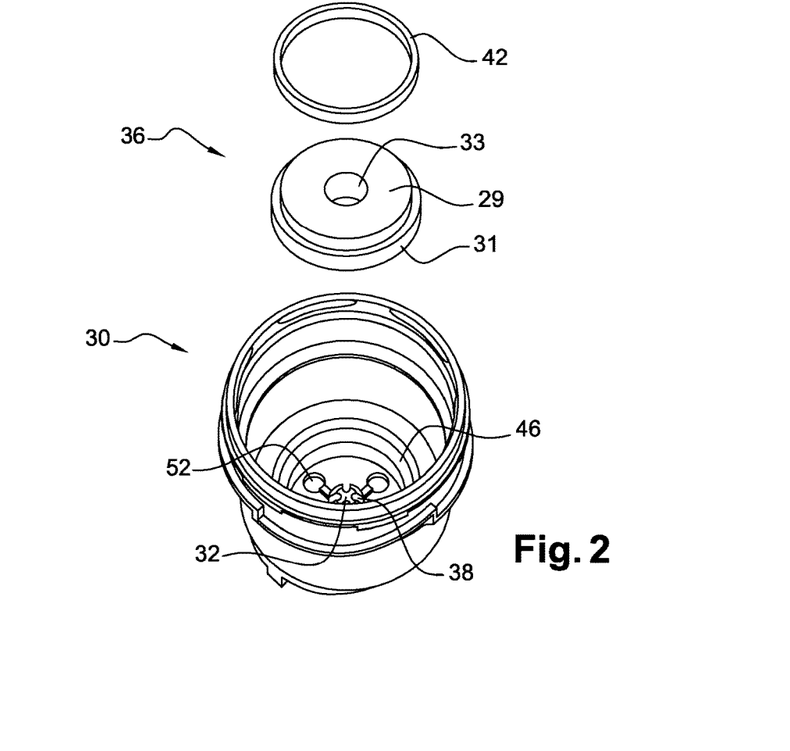
FIG. 2 is an exploded perspective view of the interior of the inner casing of the protective cap, of the absorption pad and of the support, of the device of FIG. 1.

FIGS. 1 and 2 show a first embodiment of a liquid-dispensing device 10. The device 10 is similar to that described in the publication FR 2 988 015. The device 10 is, in FIG. 1, in the hermetic closure configuration. In this non-limiting example, the device 10 is a device for dispensing liquid in drop form.

The device 10 comprises a protective cap 12 and a dispensing end piece 14 which is intended to be mounted on the neck of a tank (not represented), for example by screwing. This tank is a liquid storage tank, for example for storing pharmaceutical liquid such as ophthalmic liquid. The tank is deformable, so as to dispense the liquid by pressure, on the part of a user, on the body of the tank, the latter being able to exhibit a certain elasticity to resume its initial form after the pressure exerted by the user, which generates low pressure in the tank.

The dispensing end piece 14 comprises a membrane 18, or valve 18, forming a non-return valve, a valve support 26 and a top casing 24. The valve 18 delimits, with the valve support 26, a channel 20 for dispensing liquid from the tank. This channel 20 emerges on a flared part, forming drop formation means 34, produced in the valve 18 for the formation of drops, defining a liquid-dispensing opening 22. The valve 18 is configured in such a way as to be able to assume a configuration of passage of liquid, during which liquid can reach the dispensing opening 22, and a configuration of blocking of the liquid, during which the valve 18 is pressed against the top end of the valve support 26, thus blocking the passage of liquid.

Figure 5:
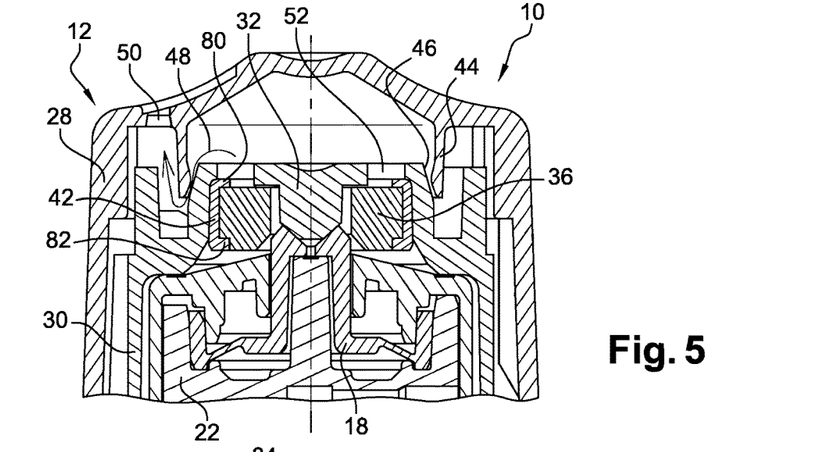
FIG. 5 is a view similar to FIG. 1 of a device according to a third embodiment in the ventilation configuration.

There now follows a description of the protective cap 12, mounted on the dispensing end piece 14, preferably by screwing. The protective cap 12 comprises, in this example, an outer casing 28 and an inner casing 30. These inner and outer casings 30, 28 are coaxial, secured to one another while being mounted mobile relative to one another in rotation and in longitudinal translation, between a first configuration, corresponding to a configuration of hermetic closure of the device 10, visible in FIG. 1, and a second configuration corresponding to a configuration of ventilation of the device 10. As illustrated in FIG. 5, in the ventilation configuration, an evaporation path 48 is open between the absorption pad 36 described hereinbelow and the outside of the device 10, such that residual liquid absorbed by this absorption pad 36 can evaporate. The inner casing 30 further comprises a residual liquid expulsion form 32 which would be located in or in the vicinity of the dispensing opening 22. This expulsion form 32 is situated in the immediate vicinity of and facing the dispensing opening 22.

The expulsion form 32 is also, in this example, a form for immobilizing the valve 18 in the position of blocking of the liquid when the protective cap 12 is mounted on the device 10. For example, the expulsion form 32 is a slug whose general form complements the drop formation means 34, produced in the valve 18, for example the expulsion form 32 is frustoconical. Thus, the expulsion form 32 ensures an immobilization of the valve 18 by jamming the latter against the valve support 26.

The protective cap 12 comprises a residual liquid absorption pad 36, fixed onto the protective cap 12 via a support 42 which is itself fixed, in this example, onto the inner casing 30 of the protective cap 12.

The absorption pad 36 is of substantially annular form. It is arranged around the residual liquid expulsion form 32. It has an orifice 33 receiving the expulsion form 32 of the inner casing 30 of the protective cap 12. This orifice 33 has a generally cylindrical form and can be of variable diameter. It can also be of frustoconical form and have, on the surface, possible reliefs and/or hollows. For example, the absorption pad 36 has a diameter of 10 mm+/−0.20 mm and the orifice 33 arranged at the center has a diameter of 4 mm+/−0.15 mm.

The section of the ring of the absorption pad 36 is of substantially rectangular form. One of the corners of the inner face of the absorption pad 36 could possibly be beveled and complement the form of the valve 18. Advantageously, the two corners of the inner face could be beveled, the absorption pad 36 can therefore be fixed onto the support 42 without preference in one direction or in the other.

The absorption pad 36 can comprise one or more parts of different forms and/or dimensions. In the example illustrated in FIG. 1, the absorption pad 36 consists of two parts, a first part 31 of generally annular form, of a greater diameter than a second part 29, also of generally annular form, surrounded by the support 42.

Advantageously, the absorption pad 36 can have no contact with the valve 18 in order to avoid contacts between the residual liquid present in the absorption pad 36 and the valve 18 when the protective cap 12 is mounted on the device 10.

Also advantageously, the absorption pad 36 can have no contact with the inner casing 30 of the protective cap 12 in order to avoid friction between the protective cap 12 and the absorption pad 36 responsible for generating particles. It will therefore be understood that the lateral edge 74 of the absorption pad 36 is spaced apart from centering outlines of the absorption pad 36 borne by the support 42 in the protective cap 12, the spacing means for the lateral edge of the absorption pad 36 are borne by the support 42, for example by the lateral walls of the support 42.

The absorption pad 36 advantageously comprises a porous material comprising one or more hydrophilic materials. The absorption pad 36 can also be a multilayer pad, in combination with or as an alternative to the case in which it comprises a porous material. The material of the absorption pad 36 can comprise woven or unwoven materials. It can for example comprise hydrophilic cotton, polyethylene (PE) that has undergone a hydrophilic treatment, polyethylene terephthalate (PET) that has undergone a hydrophilic treatment, a poly(vinyl acetate) (PVA) foam or a mixture of a number of hydrophilic materials. According to a particularly advantageous variant, the absorption pad 36 is made of a material comprising EVA (ethylene vinyl acetate).

The support 42, on which the absorption pad 36 is fixed, has a generally annular form. Its section is of substantially rectangular form. It can be continuous or discontinuous, and can comprise reliefs or hollows which would make it possible for example to fix it onto the inner casing 30 of the protective cap 12. Advantageously, it is arranged on the perimeter of the absorption pad 36 and is in direct contact with the inner casing 30 of the protective cap 12. More particularly in the example, it is positioned on the perimeter of the second part 29 of the absorption pad 36, which gives the assembly a greater diameter than the diameter of the first part 31 of the absorption pad 36, advantageously making it possible to return to contact with the inner casing 30 of the protective cap 12 and thus avoiding having the absorption pad 36 taken as a whole rub against this wall of the inner casing 30. The support 42 advantageously comprises a stronger material than the material of the absorption pad 36. The support 42 can be made of plastic material, such as polyethylene, treated or untreated.

The method for assembling the device 10 will now be described.

The absorption pad 36 and the support 42 are first of all assembled, advantageously by overmolding or by any other mechanical clamping means. In this way, few particles, even no particles at all, are generated in the device 10. In order to hold the absorption pad 36 on the support 42, it is also possible to envisage placing the absorption pad 36 on the support 42.

Then, the assembly is added into the protective cap 12. More particularly, the support 42 is fixed inside the inner casing 30, in such a way that the absorption pad 36 is located around the expulsion form 32 of the valve 18 once the protective cap 12 is mounted, without being in contact with the transverse edges of the inner casing 30 of the protective cap 12. The outer casing 28 is then mounted on the inner casing 30, for example by screwing, so that the outer casing 28 can no longer be separated from the inner casing 30. It will be understood that the outer casing 28 can be assembled with the inner casing 30 before the insertion of the support 42 and of the absorption pad 36. Before the absorption pad 36 and the support 42 are added into the protective cap 12, it is possible, particularly advantageously, to perform a step of blowing of compressed air over the assembly of the absorption pad 36 and of the support 42, so as to clean them of all the particles which might have been deposited. Then, the protective cap 12 is ready to be mounted by screwing onto the dispensing end piece 14, then, once the tank is filled with the liquid to be dispensed, the assembly formed by the dispensing end piece 14 and the protective cap 12 is screwed onto the neck of the tank. The device 10 is ready to be used.

The first configuration, called configuration of storage or of hermetic closure of the device 10, is represented in FIG. 1, such that there is no possible communication between the absorption pad 36 and the outside of the device 10. In this configuration, there is no communication between air passage orifices 52 of the inner casing 30 and air passage orifices 50 of the outer casing 28. In effect, a crown ring 44 of the outer casing 28 forms, with a surface 46 of the inner casing 30, a means for closing the evaporation path 48. In this embodiment, this surface 46 is conical and borne by a part of the inner casing 30 which also forms a centering outline for the absorption pad 36 in the protective cap 12, in this case in the inner casing 30.

Upon first use, the user unscrews the protective cap 12. He or she grips the outer casing 28 in one hand and the tank in the other hand. He or she rotates the outer casing 28 relative to the inner casing 30. The rotational movement applied by the user to the device 10 generates a longitudinal translational movement of the outer casing 28 relative to the inner casing 30, to a ventilation configuration. In this ventilation configuration, represented in FIG. 5, by virtue of the longitudinal displacement of the outer casing 28 relative to the inner casing 30, the crown ring 44 of the outer casing 28 no longer cooperates with the surface 46 of the inner casing 30, so that a space is created between the crown ring 44 and the surface 46, and therefore the residual liquid evaporation path 48 is open between the absorption pad 36 and the outside of the device 10.

Between two uses, the user screws the protective cap 12 back onto the dispensing end piece 14. When the cap 12 is mounted on the dispensing end piece 14, the expulsion form 32 cooperates with the valve 18, in particular with the drop formation means 34. Furthermore, this expulsion form 32 comprises grooves 38 which delimit, with the valve 18, a discharge pathway 40 for the residual liquid contained in the drop formation means 34. This discharge pathway 40 makes it possible to discharge the residual liquid to the absorption pad 36, in which it is absorbed. Then, the liquid absorbed by the absorption pad 36 can evaporate out of the device 10 through the evaporation path 48 that is open between the absorption pad 36 and the outside of the device 10. In effect, the outer casing 28 and the inner casing 30 each comprise means for locking the device 10 in the ventilation configuration, so that, when the user screws the protective cap 12 back onto the device 10, the evaporation path 48 remains open between the absorption pad 36 and the outside of the device 10.

There is therefore no residual liquid stagnating in the drop formation means 34 and the formation of solid residue of the active principle that could result in the delivery of an overdose upon the delivery of a drop or the delivery of solid particles in suspension in the drop upon the next use of the device 10 is avoided.

Figure 3:
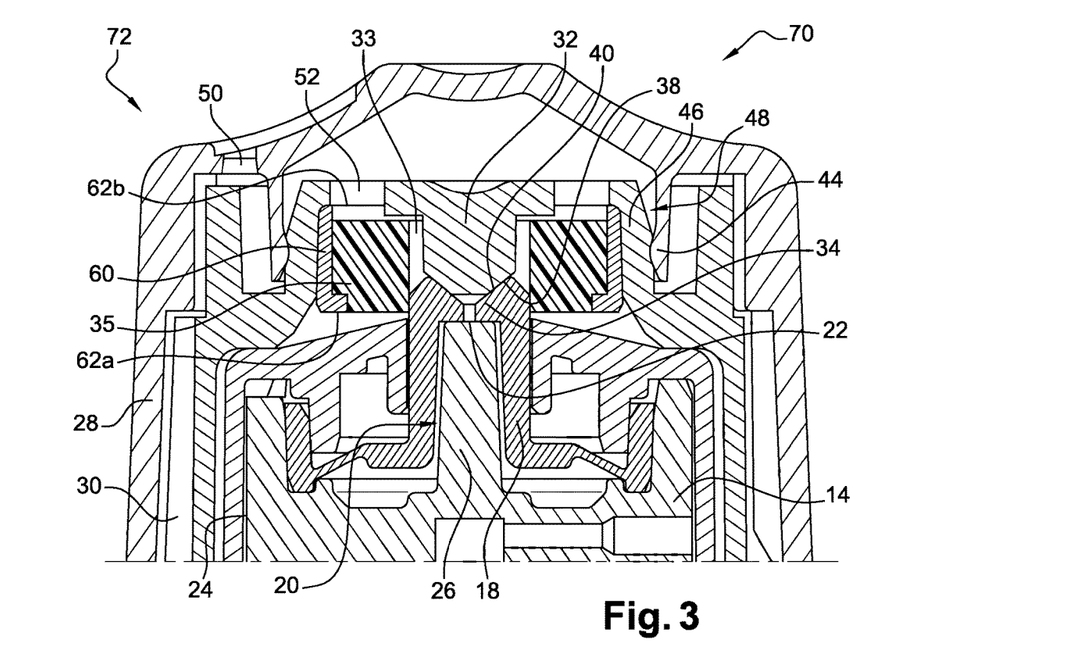
FIG. 3 is a view similar to FIG. 1 of a device according to a second embodiment.
Figure 4:
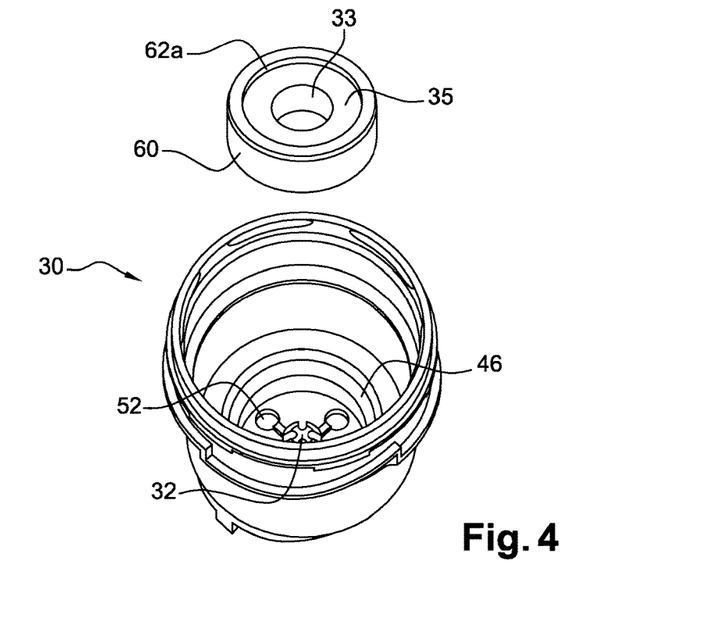
FIG. 4 is an exploded perspective view of the interior of the inner casing of the protective cap, of the absorption pad and of the support, of the device of FIG. 3.

FIGS. 3 and 4 show a second embodiment of the liquid-dispensing device 70, similar to the device 10 of FIG. 1. In the following description, the elements that are common to the different embodiments are identified by the same numeric references. This device 70 is also in hermetic closure configuration.

In this example, the protective cap 72 comprises an absorption pad 35 in a single piece and a support 60 onto which the absorption pad 35 is fixed. The absorption pad 35 is of generally annular form, 10 mm+/−0.20 mm in diameter, and has an orifice 33 allowing the passage of the expulsion form 32 with a diameter of 4 mm+/−0.15 mm. The support 60 extends, in this example, over the entire height of the absorption pad 35. It also has a part 62 that can at least partially cover a face of the absorption pad 35. In this example, a part 62b of the support 60, intended to come into abutment against the bottom of the inner casing 30 of the protective cap 72, extends over the entire top peripheral face of the absorption pad 35. In this way, advantageously, the absorption pad 35 does not enter into contact with the inner casing 30 and any friction likely to generate particles is thus avoided. The part 62a of the support 60, located on the side of the valve 18, partially covers the surface of the absorption pad 35 in such a way that the surface of the absorption pad 35, free of support, can come against the valve 18 and serve its purpose of absorption of the residual liquid present on the valve 18 after use of the device 70 and replacement of the protective cap 72.

FIGS. 5 to 13 and 15 illustrate additional embodiments of the device 10. Hereinbelow, the elements common to the different embodiments are identified by the same numeric references as those of FIGS. 1 and 2.

In the embodiment of FIG. 5, the device 10 is in ventilation configuration such that the residual liquid evaporation path 48 is open between the absorption pad 36 and the outside of the device 10.

The support 42 extends over the entire height of the absorption pad 36. It also has a top axial abutment 80 and a bottom axial abutment 82 which, by cooperation with the absorption pad 36, immobilize the absorption pad 36 in the support 42.

It will moreover be noted that the top axial abutment 80 comes into abutment in the inner casing 30. Thus, when this assembly is added into the inner casing 30, the support 42 is pressed in until the top axial abutment 80 abuts in the inner casing 30. It is then observed that the absorption pad 36 does not make any contact with the inner casing 30 while, however, being immobilized in this inner casing 30.

The support 42 can be fixed onto the absorption pad 36 by overmolding of the support 42.

Figure 6:
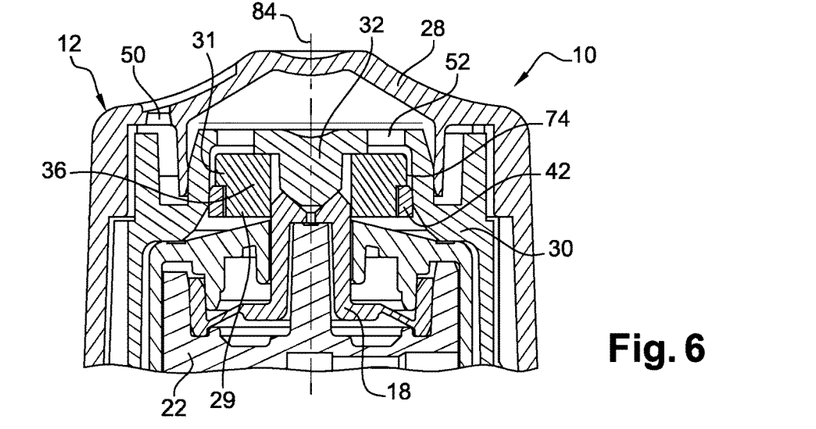
FIGS. 6 to 13 and 15 are views similar to FIG. 1 of a device according to other embodiments.

The embodiment of the device 10 of FIG. 6 is similar to the embodiment of FIG. 1. It differs therefrom in that the absorption pad 36 is placed on the support 42. There is therefore a space between the support 42 and the second part 29 of the absorption pad 36. However, this space is such that if the absorption pad 36 moves slightly in a plane at right angles to the central axis 84 of the device 10, the lateral edge 74 of the absorption pad 36 still remains spaced apart from the inner walls of the inner casing 30.

It will also be noted that the absorption pad 36 is immobilized axially by being jammed between the support 42 and the bottom of the inner casing 30.

Figure 7:
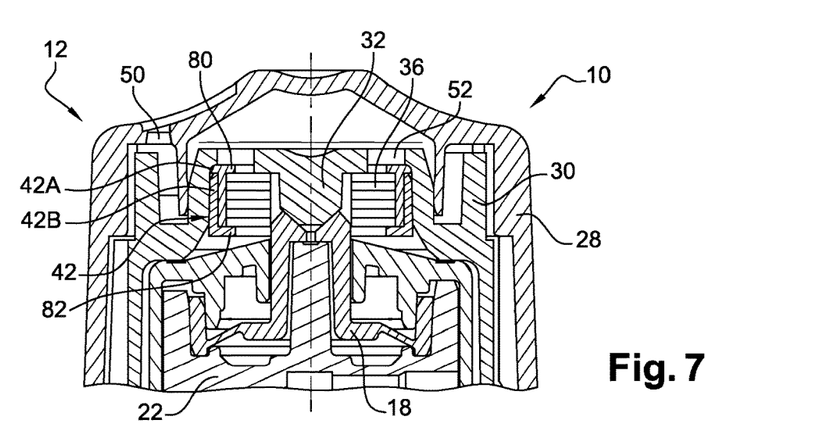

In the embodiment of FIG. 7, the support 42 comprises a top part 42A and a bottom part 42B, fitted into one another, respectively defining the top 80 and bottom 82 axial abutments. The top axial abutment 80 comes into abutment in the inner casing 30. It can also be seen that the absorption pad 36 is composed of a plurality of pad layers stacked axially on top of one another.

Figure 8:
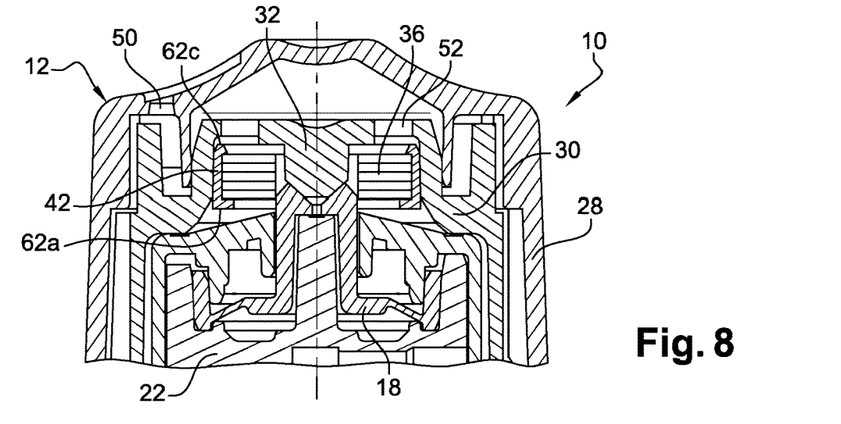

The embodiment of FIG. 8 is similar to the embodiment of FIG. 3. It differs therefrom in that the absorption pad 36 is here produced by an axial stacking of pad layers and in that the support 42 comprises a part 62c that is located opposite the side of the valve 18 and partially covers the surface of the absorption pad 36 in such a way that the pad layers of the absorption pad 36 are axially blocked between the parts 62a and 62c.

Figure 9:
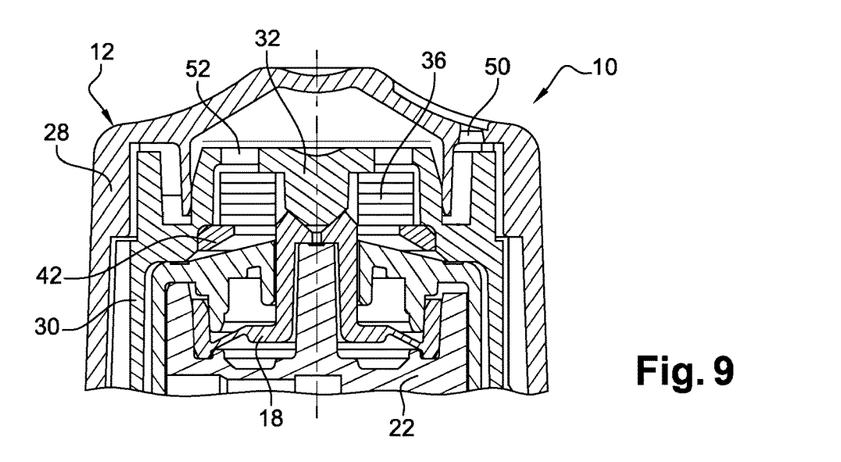

The embodiment of FIG. 9 differs from the preceding embodiments in that the support 42 does not form a ring around the absorption pad 36. In this embodiment, the support 42 forms a plateau on which the absorption pad 36 is placed, in the present case the stacking of absorption pad layers. The support 42 is then snap-fitted onto the inner casing 30 so as to fix the assembly formed by the support 42 and the absorption pad 36 in the inner casing 30.

Figure 10:
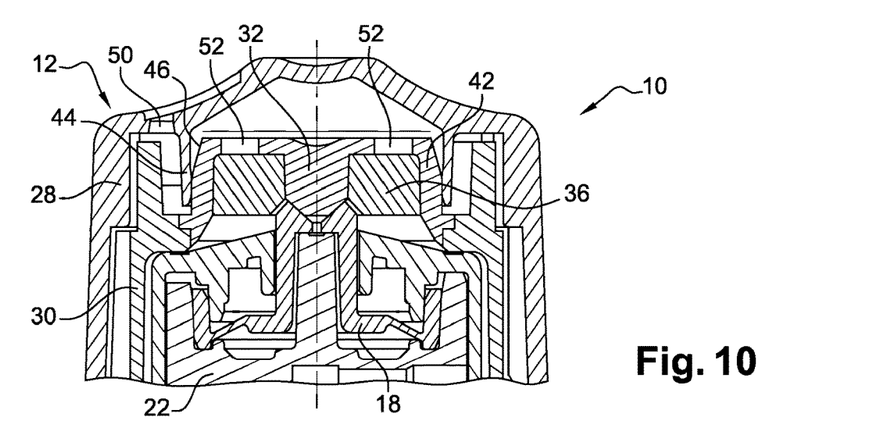

In the embodiment of FIG. 10, the support 42 bears the surface 46 which cooperates with the crown ring 44 of the outer casing 28 in order to close the residual liquid evaporation path 48 in the configuration of hermetic closure of the device 10. The support 42 also comprises the residual liquid expulsion form 32. The lateral edge 74 of the absorption pad 36 does not therefore come into contact with the inner casing 30 when the assembly formed by the absorption pad 36 and the support 42 is added into the centering outline of the absorption pad 36 borne by the inner casing 30 of the protective cap 12. There is therefore no or little formation of particles when the support 42 provided with the absorption pad 36 is added into the protective cap 12. It will also be noted that the support 42 is added from the outside of the inner casing 28, that is to say from above.

The embodiments of FIGS. 11 to 16 represent a device 10 whose protective cap 12 comprises only a single casing 27 similar to the inner casing 30 of the embodiments previously described and a spring element 83, elastically deformable, capable of stressing the valve 18 to its blocking position.

Figure 11:
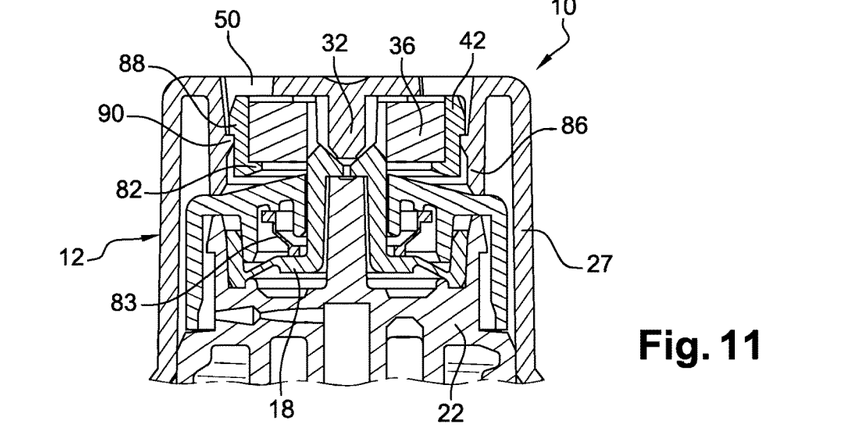

In the embodiment of FIG. 11, the protective cap 12 comprises air passage orifices 50 from the absorption pad 36 to the outside of the device 10. It will therefore be understood that the device 10 is represented in the ventilation configuration. The bottom of the protective cap 12 comprises an inner crown ring 86 which forms the centering outline for the absorption pad 36 in the protective cap 12 and the residual liquid expulsion form 32.

The support 42 comprises a bottom axial abutment 82 on which the absorption pad 36 rests. The support 42 bears, on its outer radial surface, snap-fitting means 88 which cooperate with complementary snap-fitting means 90 borne by the inner crown ring 86 so as to fix the assembly formed by the support 42 and the absorption pad 36 in the protective cap 12.

Figure 12:
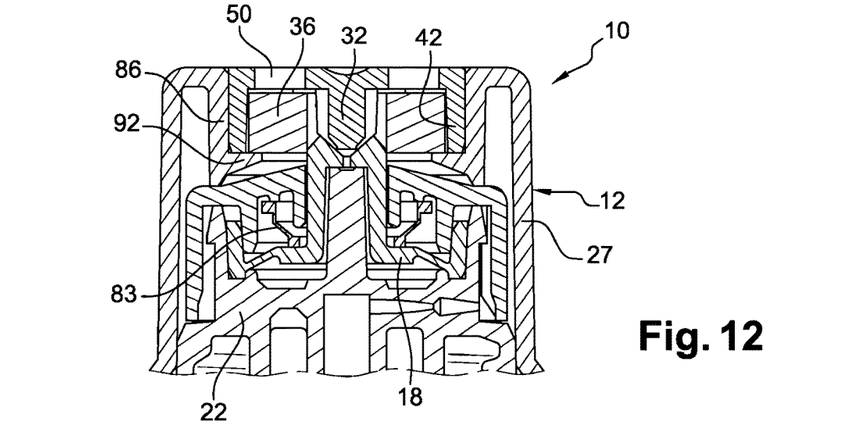
Figure 13:
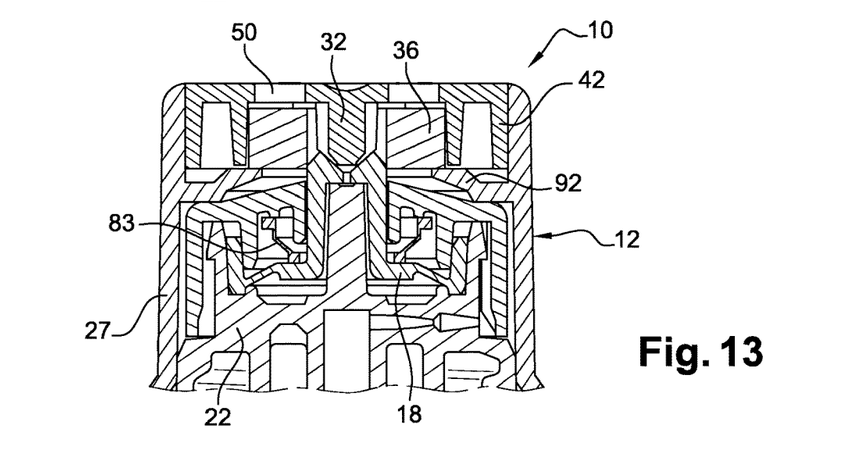
Figure 15:
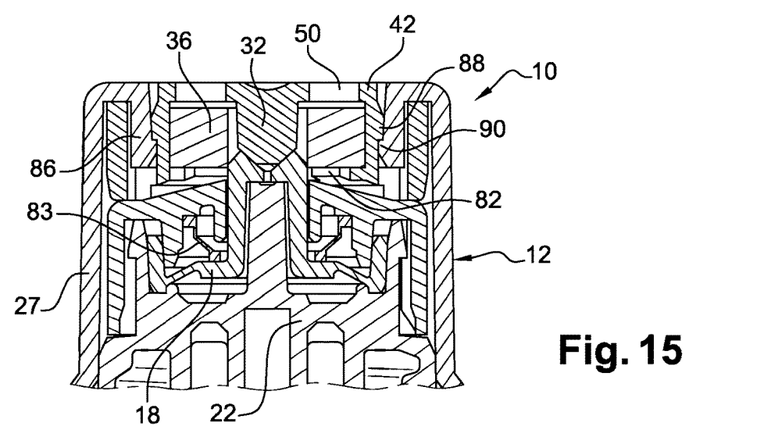

In the embodiments of FIGS. 12, 13 and 15, the support 42 comprises the air passage orifices 50 from the absorption pad 36 to the outside of the device 10 and the residual liquid expulsion form 32.

In the embodiments of FIGS. 12 and 13, the support 42 is added into the protective cap 12 from the outside, that is to say from above, of the protective cap 12, unlike the embodiments of FIGS. 1 to 9, 11 and 15.

In these embodiments, the support 42 is fixed in the protective cap 12 by mechanical clamping. Moreover, it will be noted that the protective cap 12 comprises an axial abutment 92 which allows for the positioning of the support 42 relative to the protective cap 12.

In the embodiment of FIG. 12, the centering outline of the absorption pad 36 in the protective cap 12 is formed by the inner crown ring 86 whereas, in the embodiment of FIG. 13, the centering contour of the absorption pad 36 in the protective cap 12 is formed by the lateral wall of the protective cap 12.

Figure 14:
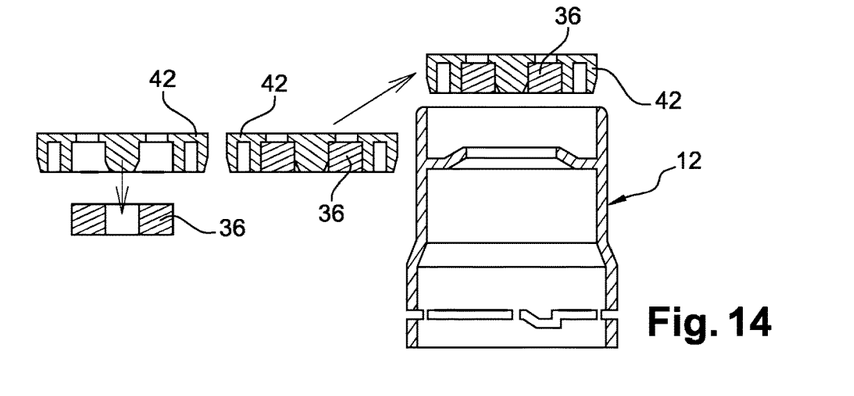
FIG. 14 is a cross-sectional view illustrating the method of assembling the pad, the support and the protective cap of the embodiment presented in FIG. 13.

FIG. 14 illustrates the different steps of the method for assembling the absorption pad 36 and the support 42 with the protective cap 12. Unlike what has been described previously, it can be seen that the assembly formed by the absorption pad 36 and the support 42 is added through the top of the protective cap 12.

In the embodiment of FIG. 15, the support 42 is added through the interior of the protective cap 12 and is fixed therein by snap-fitting, by cooperation of snap-fitting means 88, 90 respectively borne by the support 42 and the internal crown ring 86 of the protective cap 12. The support 42 further comprises a plurality of bottom axial abutments 82 which are passed by force upon insertion of the absorption pad 36 into the support 42.

Figure 16:
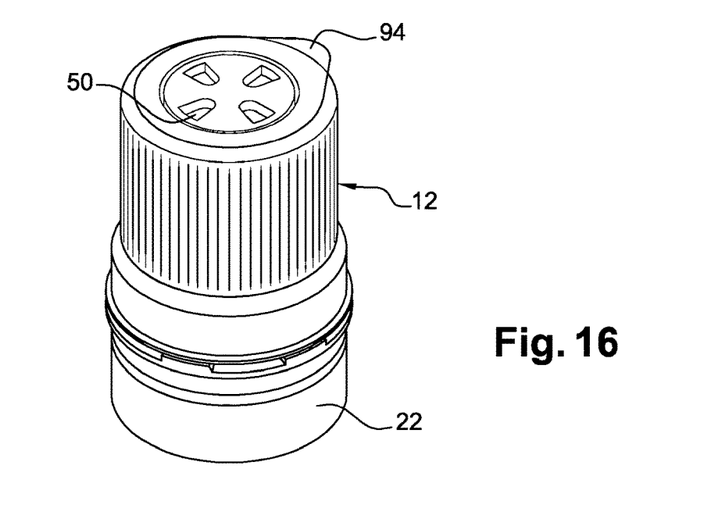
FIG. 16 is a perspective view of the device of FIG. 15 in the hermetic closure configuration.

FIG. 16 illustrates the device 10 of FIG. 15 in the configuration of hermetic closure of the device 10 before first use. The protective cap 12 comprises a membrane seal 94 closing the air passage orifices 50 and therefore the residual liquid evaporation path 48 before first use. The membrane seal 94 is removable, preferably disposable, and is added onto the protective cap 12. Upon first use, the user removes the membrane seal 94 from the device 10 which passes from the configuration of hermetic closure to the configuration of ventilation.

It will be understood that the invention is not limited to the examples presented above and that modifications will become clearly apparent to those skilled in the art.

The invention claimed is:

1. A liquid-dispensing device, comprising:
   an end piece with a liquid-dispensing opening removably attachable to a neck of a tank;
   a removable protective cap for covering the liquid-dispensing opening, the protective cap comprising an outer casing and an inner casing connected to one another and removable together to uncover the liquid-dispensing opening, the protective cap being provided with a residual liquid absorption pad, made of an absorbent material, the absorption pad being fixed onto a support made of a stronger material than the absorption pad, the support being distinct from, such that the support is not integrally formed with, the protective cap and also fixed in the inner casing of the protective cap.

2. The device according to claim 1, in which the support is made of a plastic material.

3. The device according to claim 1, in which the support has an annular form.

4. The device according to claim 1, in which the support extends over the entire height of the absorption pad.

5. The device according to claim 1, in which the absorption pad is overmolded on the support.

6. The device according to claim 1, in which the absorption pad is made of a porous material.

7. The device according to claim 1, in which the absorption pad is made of a material comprising EVA (ethylene vinyl acetate).

8. The device according to claim 1, in which the absorption pad comprises at least two stacked pad layers.

9. The device according to claim 1, in which the absorption pad is kept immobile between two axial abutments of the support cooperating with the absorption pad.

10. The device according to claim 9, in which the support comprises two parts fitted into one another, each part defining an axial abutment.

11. The device according to claim 1, comprising a residual liquid expulsion form situated in the immediate vicinity of and facing the dispensing opening and borne by the protective cap or the support, when the protective cap is mounted on the device.

12. The device according to claim 1, that can take, when the protective cap is mounted on the device, a configuration of hermetic closure of the device, before its first use, in which a residual liquid evaporation path is closed between the absorption pad and the outside of the device, and a configuration of ventilation of the device, in which the residual evaporation path is open between the absorption pad and the outside.

13. The device according to claim 12, wherein the outer casing the inner casing are mounted mobile relative to one another between a first configuration, corresponding to the configuration of hermetic closure of the device, and the configuration of ventilation of the device.

14. The device according to claim 12, in which the protective cap comprises air passage orifices and a seal closing the residual liquid evaporation path before the first use.

15. A method for assembling a device according to claim 1, during which the absorption pad and the support are first of all assembled, then the assembly is added into the protective cap.

16. The method for assembling a device according to claim 15, further comprising a step of blowing of compressed air over the assembly of the absorption pad and the support, before they are added into the protective cap.

17. The device according to claim 2, in which the support is made of polyethylene.

18. The device according to claim 1, wherein the absorption pad is least axially supported in the inner casing of the protective cap by the support.

19. The device according to claim 1, wherein the absorption pad is retained in the protective cap only by interaction between support and an interior surface of the inner casing of the protective cap.

* * * * *

UNITED STATES PATENT AND TRADEMARK OFFICE
CERTIFICATE OF CORRECTION

PATENT NO. : 10,160,577 B2  
APPLICATION NO. : 15/127677  
DATED : December 25, 2018  
INVENTOR(S) : Thierry Decock et al.

Page 1 of 1

It is certified that error appears in the above-identified patent and that said Letters Patent is hereby corrected as shown below:

On the Title Page

Item (72)
"Thierry Decock, Lyons (FR)" should be changed to -- Thierry Decock, Lyon (FR) --

Item (72)
"Benjamin Quaglia, Lyons (FR)" should be changed to -- Benjamin Quaglia, Lyon (FR) --

Signed and Sealed this
Twenty-sixth Day of February, 2019

Andrei Iancu
*Director of the United States Patent and Trademark Office*